United States Patent
Parr et al.

(10) Patent No.: US 9,578,877 B2
(45) Date of Patent: Feb. 28, 2017

(54) COCOALKYLPOLYAMINE ALKOXYLATES AS AGENTS FOR HIGH STRENGTH HERBICIDE COMPOSITIONS

(75) Inventors: Rodney Walter Parr, Doncaster (AU); Dilek Saylik, Meadow Heights (AU)

(73) Assignee: HUNTSMAN CORPORATION AUSTRALIA PTY LIMITED, Brooklyn (AU)

(*) Notice: Subject to any disclaimer, the term of this patent is extended or adjusted under 35 U.S.C. 154(b) by 143 days.

(21) Appl. No.: 13/383,216

(22) PCT Filed: Jul. 22, 2010

(86) PCT No.: PCT/AU2010/000932
§ 371 (c)(1),
(2), (4) Date: Jan. 10, 2012

(87) PCT Pub. No.: WO2011/009171
PCT Pub. Date: Jan. 27, 2011

(65) Prior Publication Data
US 2012/0108432 A1    May 3, 2012

Related U.S. Application Data

(60) Provisional application No. 61/227,544, filed on Jul. 22, 2009.

(51) Int. Cl.
| | | |
|---|---|---|
| *A01N 25/30* | (2006.01) | |
| *A01N 25/02* | (2006.01) | |
| *A01N 33/12* | (2006.01) | |
| *A01N 41/04* | (2006.01) | |
| *A01N 47/06* | (2006.01) | |
| *A01N 57/20* | (2006.01) | |

(52) U.S. Cl.
CPC .......... *A01N 25/30* (2013.01); *A01N 25/02* (2013.01); *A01N 33/12* (2013.01); *A01N 41/04* (2013.01); *A01N 47/06* (2013.01); *A01N 57/20* (2013.01)

(58) Field of Classification Search
CPC ........ A01N 25/30; A01N 25/02; A01N 31/02; A01N 33/04; A01N 33/08; A01N 33/12; A01N 57/20; A01N 2300/00; A01N 41/04; A01N 47/06
See application file for complete search history.

(56) References Cited

U.S. PATENT DOCUMENTS

| | | | |
|---|---|---|---|
| 5,750,468 A * | 5/1998 | Wright et al. | 504/206 |
| 2005/0080089 A1* | 4/2005 | Tiedink et al. | 514/254.07 |
| 2007/0004595 A1* | 1/2007 | Scherl | 504/206 |
| 2009/0093505 A1* | 4/2009 | Bylemans et al. | 514/275 |
| 2012/0157313 A1* | 6/2012 | Zhu et al. | 504/206 |

FOREIGN PATENT DOCUMENTS

| | | |
|---|---|---|
| EP | 0290416 | 3/2005 |
| GB | 2233229 | 1/1991 |
| WO | 01/89302 | 11/2001 |
| WO | 02/098221 | 12/2002 |

OTHER PUBLICATIONS

International Search Report and Written Opinion regarding corresponding application No. PCT/AU2010/000932, dated Sep. 8, 2010.

* cited by examiner

*Primary Examiner* — John Pak
*Assistant Examiner* — Nathan W Schlientz
(74) *Attorney, Agent, or Firm* — Huntsman International LLC

(57) ABSTRACT

Embodiments of the present invention disclose an agricultural composition having an agrochemical active ingredient and at least one cocoalkylpolyamine alkoxylate agent.

12 Claims, No Drawings

COCOALKYLPOLYAMINE ALKOXYLATES AS AGENTS FOR HIGH STRENGTH HERBICIDE COMPOSITIONS

CROSS-REFERENCE TO RELATED APPLICATIONS

This application is the National Phase of International Application PCT/AU2010/000932, filed Jul. 22, 2010 which designated the U.S. and which claims priority to U.S. provisional application No. 61/227,544 filed Jul. 22, 2009. The noted applications are incorporated herein by reference.

STATEMENT REGARDING FEDERALLY SPONSORED RESEARCH OR DEVELOPMENT

Not applicable.

BACKGROUND OF THE INVENTION

Field of the Invention

The present invention relates generally to agricultural compositions, in particular novel formulations utilizing cocoalkylpolyamine alkoxylates as agents for high strength herbicide compositions.

Background of the Invention

The use of alkyldiamine ethoxylates in glyphosate have been explored previously by a number of scientists. Wyrill and Burnside, Weed Science Vol. 25 (1977), 275-287, conducted a study of the effects of different agents including tallowpropyldiamine ethoxlyates on the herbicidal action of glyphosate. Some classes of agents were more effective than others in enhancing the herbicidal effect of glyphosate (in particular as a solution of the isopropylamine salt). In the early 1990's, Rhone Poulenc disclosed an application of liquid herbicide formulation containing N-phosphonomethylglycine and diamine surfactant (DE 4019362 A1 19910103). According to the abstract of the application, the most efficacious formulation of their invention comprised of isopropylammonium N-phosphonomethylglycine otherwise known as isopropylamine glyphosate at 100 grams per liter and tallowpropyldiamine ethoxylate which contained 3 ethylene oxide units.

Users of aqueous concentrate herbicides and fertilizers find advantages in being supplied with high concentration formulations. In the case of glyphosate, advantages in shipping and storage can be gained by the use of formulations containing high concentrations of the glyphosate acid compared to the conventionally used concentrations. Unfortunately few agents are available which are compatible in such higher strength formulations.

As well, incorporation of aqueous solutions of fertilizers alone or in combination with pesticides and water soluble herbicides in concentrated form is often problematic because of their high ionic strength and so it is desirable to make agents and other additives compatible with them. By "compatible", it is meant that combinations of agents and agrochemicals are made homogeneous and do not separate into two or more distinct continuous phases. Therefore there is a need for stable, high concentration formulations of water soluble herbicides and fertilizers.

BRIEF SUMMARY OF SOME OF THE PREFERRED EMBODIMENTS

Embodiments of the present invention disclose an agricultural composition having an agrochemical active ingredient and at least one cocoalkylpolyamine alkoxylate agent.

In an aspect of the present invention, the at least one cocoalkylpolyamine alkoxylate agent has a structure of formula (I):

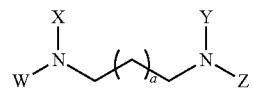

wherein W is a coco hydrocarbyl group, X and Y can be alkylene oxide or alkylene oxide substituted alkylamino group or a combination thereof, Z is independently selected from the group consisting of an ethylene oxide unit, a propylene unit and a combination thereof and a is an integer from 0 to 2.

In an aspect of the present invention, the at least one cocoalkylpolyamine alkoxylate agent has a structure of formula (II):

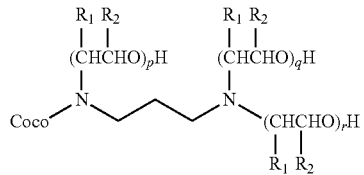

wherein $p+q+r$ is any value from about 1 to about 8; Coco is a coco hydrocarbyl group; and wherein $R_1$ and $R_2$ are each independently selected from the group consisting of: a H and a $C_1$-$C_4$ alkyl group.

In an aspect of the present invention, the at least one cocoalkylpolyamine alkoxylate agent is a derivatized form selected from the group consisting on an amine oxide derivative, a quaternary amine derivative, a betaine derivative, a phosphate derivative, a sulfate derivative, a carboxylic acid derivative, and a combination thereof.

In an aspect of the present invention, the agrochemical active ingredient comprises glyphosate or salt thereof selected from the group consisting of an ammonium, an alkylamine, an alkanolamine, an alkylsulfonium, an alkali metal and a combination thereof.

In an aspect of the present invention, the agrochemical active ingredient comprises a water soluble herbicide selected from the group consisting of: a bipyridyl herbicide, a phenoxy ester herbicide, a pyridinylphenoxy herbicide, a salt thereof, and a combination thereof.

In an aspect of the present invention, the agrochemical active ingredient comprises a water soluble fertilizer.

In an aspect of one present invention, the composition further includes at least one additive. The additive may be an antifoaming agent, a compatibilizing agent, a sequestering agent, a neutralizing agent, a dye, an odorant, a penetration aid, a wetting agent, a spreading agent, a thickening agent, a freeze point depressant, a humectant, a conditioner, an antimicrobial agent, a crop oil, and a combination thereof.

In an aspect of the present invention, the agrochemical active ingredient is at least 360 grams acid equivalent per liter (gae/L).

In an aspect of the present invention, the agrochemical active ingredient is at least 450 grams acid equivalent per liter (gae/L).

In an aspect of the present invention, the agrochemical active ingredient is at least 540 grams acid equivalent per liter (gae/L).

In an aspect of the present invention, the agrochemical active ingredient is at least 600 grams acid equivalent per liter (gae/L).

Embodiments of the present invention disclose a method of making a high strength aqueous solution comprising the steps of contacting an agrochemical active ingredient and at least one cocoalkylpolyamine alkoxylate agent.

Embodiments of the present invention disclose a method of treatment of vegetation comprising the step of contacting the agricultural composition to vegetation.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

DETAILED DESCRIPTION OF THE PREFERRED EMBODIMENTS

Embodiments of the present invention include an agrochemical active ingredient and at least one cocoalkylpolyamine alkoxylate agent. Agrochemical active ingredients may include water soluble herbicides, fertilizers and combinations thereof. Water soluble herbicides and fertilizers, and their concentrations thereof, may include without limitation, glyphosate, glufosinate, pyridinylphenoxm bipyridyl (including bipyridlylquaternary ammonium salts (bipyridinium salt) such as paraquat and diquat), phenoxy esters, salts of phenoxy acids such as 2,4-dichlorophenoxyacetic acid, meta-chlorophenoxyacetic acid (MCPA), picloram, triclopyr, bromoxynil, salts thereof and combinations thereof.

As used herein, "glyphosate" means N-phosphonomethylglycine in its acid form or any agriculturally acceptable salt thereof as well as any composition or formulation containing a glyphosate herbicide. "Glyphosate herbicide" means any form of glyphosate which in aqueous solution provides glyphosate anions along with suitable cations or glyphosate acid. Examples of such suitable cations are alkali metal cations, for instance sodium and potassium, and ammonium and substituted ammonium cations that are used to form an alkali metal salt. The latter include cations derived from primary or secondary amines such as alkylamines (i.e. isopropylamine or dimethylamine), alkanolamines, and from diamines such as ethylenediamine. Glyphosate herbicide includes the isopropylamine salts of glyphosate and other agriculturally acceptable salts of glyphosate such as those disclosed in U.S. Pat. No. 3,799,758. Further, examples of agriculturally acceptable salts of glyphosate are trimethyl-sulfonium salt ("sulfosate") or aminoguanidine salts as disclosed in EP-A-0 088 180. Because glyphosate has more than one replaceable hydrogen atom, mono- and di-salts are possible, as well as mixtures of such salts. Typical glyphosate salts are the potassium, ammonium and trimethylsulphonium salts as well as the mixed alkylsulfonium and trialkylammonium salts.

As used herein, "glufosinate" means N-phosphonomethylalanine in its acid form or any agriculturally acceptable salt thereof.

In another embodiment of the present invention, the agrochemical active ingredient is a water soluble fertilizer. Suitable water soluble fertilizers may include, without limitation, inorganic and/or organic fertilizers, fertilizing salts, and mineral fertilizers such as urea, urea phosphate, urea-containing mixed fertilizers, ammonium nitrate, ammonium sulfate-nitrate, ammonium sulfate, mono- and di-ammonium phosphate, monopotassium phosphate, Chilean nitrate, potassium-ammonium phosphate, potassium chloride, potassium nitrate, potassium phosphate, potassium sulfate, sodium nitrate, nitrogenous fertilizers, potassium salts, N, P, K-compound fertilizers, N, P, K-compound fertilizers containing trace elements and combinations of such fertilizers and mineral fertilizers.

Suitable water-soluble fertilizers may also include chlorides, sulfates, or nitrates of Ca, Mg, Fe, Ni, Mn, Zn, Cu, and Co as well as Mo in the form of water-soluble molybdates and boron in the form of boric acid or boric anhydride. These fertilizers may be in complexed or partially complexed form in order to ensure water solubility. These fertilizers may be complexed with alkali metal salts of N-carboxyalkyl-amino acids. One skilled in the art will recognize other suitable water soluble fertilizers for use with this invention.

In other embodiments, the agrochemical active ingredient may include, without limitation: insecticides, fungicides, biocides, molluscicides, algaicides, plant growth regulators, anthelmintics, rodenticides, nematocides, acaricides, amoebicides, protozoacides, crop safeners and combinations thereof. Examples of such agricultural ingredients can be drawn from the Pesticide Dictionary (contained in the Farm Chemicals Handbook) or the British Crop Protection Society: Pesticides Manual, the contents of which are incorporated herein by reference. One skilled in the art, with the benefit of this disclosure, will recognize suitable water soluble agricultural ingredients and combinations thereof for use in this invention.

Embodiments of the present invention include at least one cocoalkylpolyamine alkoxylate agent. By "agent" it is also referred that it may act as an adjuvant. In an embodiment, the cocoalkylpolyamine alkoxylate agent has the structure of formula (I):

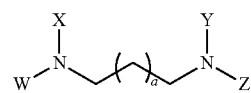

wherein W is a coco hydrocarbyl group, X and Y can be alkylene oxide or alkylene oxide substituted alkylamino group or a combination thereof, Z is independently selected from the group consisting of an ethylene oxide unit, a propylene oxide unit and a combination thereof and a is an integer from 0 to 2. In cases where Z is an ethylene oxide group, the cocoalkylpolyamine alkoxylate would be a cocoalkylpolyamine ethoxylate.

For the purposes of this disclosure, coco hydrocarbyl groups are generally defined as the alkyl or alkenyl groups obtained from the chemical modification of natural and synthetic fatty acids and their esters and particularly their naturally occurring esters with glycerol. Those skilled in the art will generally recognize that coco hydrocarbyl is a mix of carbon lengths from $C_8$-$C_{18}$ with a large concentration of carbon in the range of $C_{12}$-$C_{14}$. However, coco hydrocarbyl group compositions may have outlying carbon lengths in the ranges from about $C_6$-$C_{24}$. Coco hydrocarbyl groups may include, without limitation, caproic acid, caprylic acid, capric acid, lauric acid, myristic acid, palmitic acid, stearic acid, oleic acid, and linoleic acid.

In an embodiment, the cocoalkylpolyamine alkoxylate agent has the structure of formula (II):

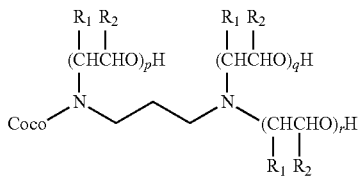

wherein p+q+r is any value from about 1 to about 8, preferably 3.5 and most preferably 7.0; Coco is a coco hydrocarbyl group; and wherein $R_1$ and $R_2$ are each independently H or a $C_1$-$C_4$ alkyl group.

In embodiments of the present invention, the at least one cocoalkylpolyamine alkoxylate agent may be a derivatized form such as amine oxide derivatives, quaternary amine derivatives, betaine derivatives, phosphate ester derivatives, sulfate derivatives, carboxylic acid derivatives and combinations thereof. Non-limiting examples of amine oxide (N-Oxide) derivatives are represented by the following formulas: wherein Coco is a coco hydrocarbyl group as in formula (II); p, q, r, $R_1$ and $R_2$ are the same values as in formula (II); and, the a, W, X, Y and Z are the same values as in formula (I):

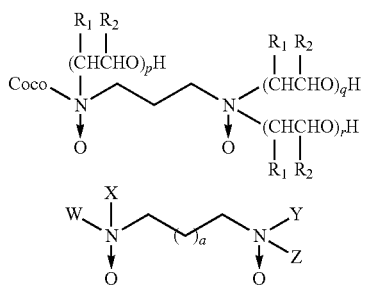

Non-limiting examples of quaternary amine derivatives are represented by the following formulas: wherein Coco is a coco hydrocarbyl group; p, q, r, $R_1$ and $R_2$ are the same values as in formula (II); Bz is a benzyl group; and, the a, W, X, Y and Z are the same values as in formula (I):

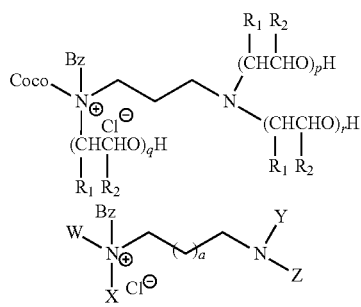

Non-limiting examples of betaine derivatives are represented by the following formulas: wherein Coco is a coco hydrocarbyl group; p, q, r, $R_1$ and $R_2$ are the same values as in formula (II); and the a, W, X, Y and Z are the same values as in formula (I):

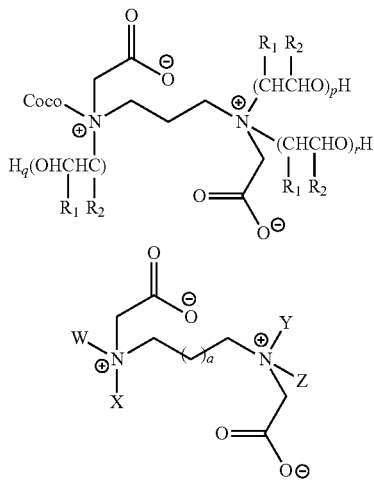

Non-limiting examples of phosphate ester derivatives are represented by the following formulas: wherein Coco is a coco hydrocarbyl group; p, q, r, $R_1$ and $R_2$ are the same values as in formula (II); and the a, W, X, Y and Z are the same values as in formula (I):

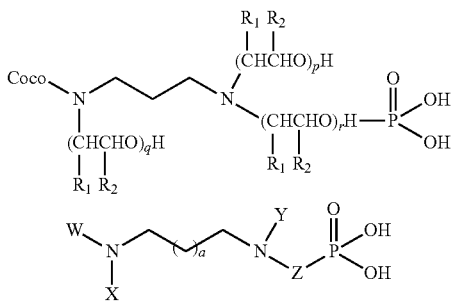

Non-limiting examples of sulfate and carboxylic acid derivatives are represented by the following formula: wherein E is a sulfate group or carboxylic acid group and wherein a, W, X, Y and Z are the same values as formula (I):

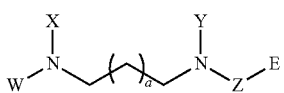

One skilled in the art, with the benefit of this disclosure, will recognize other suitable cocoalkylpolyamine alkoxylate agents for use in the present invention.

Embodiments of cocoalkylpolyamine alkoxylate agents of the present invention may be prepared by typical alkoxylation reactions known to those skilled in the art.

Embodiments of the present invention disclose an agricultural composition. A typical composition of the invention may be as follows:

| | |
|---|---|
| Agrochemical active ingredient | >360 g/L (as acid equivalent) |
| Cocoalkylpolyamine alkoxylate agent | 60-120 g/L |
| Water | to volume |

In embodiments where a greater concentration of agrochemical active ingredient is desired, the water soluble agricultural ingredient may be in any concentration higher than about 360 g/L (as acid equivalent). In other embodiments, the water soluble agricultural ingredient may be in a concentration of about 420 g/L, 450 g/L, 480 g/L, 490 g/L, 510 g/L, 517 g/L or 520 g/L. In one embodiment, the water soluble agricultural ingredient is in a concentration of about 540 g/L. In other embodiments, the concentration may be about 600 g/L. A high strength formulation may be desirable for a variety of both economic and environmental reasons such as to reduce the shipping and handling costs and to reduce the amount of packaging material that must be disposed.

In embodiments of the present invention, the use of the cocoalkylpolyamine alkoxylate agent can range from about 1% to about 15.0% by weight of the cocoalkylpolyamine alkoxylate agent in the composition, generally around 10% w/w (weight per weight) of the composition is desirable.

In embodiments of the present invention, the agrochemical active ingredient and cocoalkylpolyamine alkoxylate agent may be in the range of about 10:1 to about 1:1. In other embodiments, the agrochemical active ingredient and cocoalkylpolyamine alkoxylate agent may be in the range of about 6:1 to about 3:1.

Embodiments of the present invention may further comprise at least one additive. The at least one additive may include antifoaming agents, compatibilizing agents, sequestering agents, neutralizing agents, dyes, odorants, penetration aids, wetting agents, spreading agents, thickening agents, freeze point depressants, humectants, antimicrobial agents, crop oils, conditioners, and combinations thereof. These additives are typically diluted in water and then applied by conventional means well known to those in the art.

Embodiments of the present invention further teach a method of making a high strength aqueous solution comprising the steps of contacting an agrochemical active ingredient and at least one cocoalkylpolyamine alkoxylate agent. The composition of the present invention may be in the form of a concentrate designed to be used for addition to an agricultural spray tank.

Embodiments of the present invention also disclose a method of treatment of vegetation comprising the step of contacting the agricultural compositions of the present invention to vegetation. Herbicidal and fertilizer compositions of the present invention may be applied to plants and soils.

Embodiments of the present invention will be further illustrated by a consideration of the following examples, which are intended to be exemplary of the invention.

EXAMPLES

A number of examples have been prepared in the laboratory and screened in high load potassium glyphosate (540 g/L) formulations. These candidates were subjected to pot and field trials for evaluation of the bioefficacy function.

Example 1

Cocoalkyl-1,3-propanediamine, (Feixlang Chemicals FLTA-CO), (291.1 g, 1:09 mole) was charged to a 2 liter reactor. After three vacuum and purge cycles with nitrogen the reactor was heated to 145° C. and ethylene oxide (168.4 g, 3.83 mole) was added at a steady rate over 45 minutes. The product was cooled and discharged to give cocoalkyl-1,3-propanediamine 3.5 ethoxylate as the predominant species.

Example 2

Example 1 (442.5 g) and 50% w/w aqueous potassium hydroxide (2000 ppm) was charged to a 2 liter reactor. After three vacuum and purge cycles with nitrogen, the reactor was heated to 145° C. and ethylene oxide (116 g) was added at a steady rate over 26 minutes. The product was cooled and discharged to give cocoalkyl-1,3-propanediamine 6.0 ethoxylate as the predominant species.

Example 3

Example 2 (441.5 g) was charged to a 2 liter reactor. After three vacuum and purge cycles with nitrogen the reactor was heated to 145° C. and ethylene oxide (36.7 g) was added at a steady rate over 20 minutes. The product was cooled and discharged to give cocoalkyl-1,3-propanediamine 7.0 ethoxylate as the predominant species.

Example 4

Example 3 (354.2 g) was charged to a 2 liter reactor. After three vacuum and purge cycles with nitrogen the reactor was heated to 145° C. and ethylene oxide (27.2 g) was added at a steady rate over 27 minutes. The product was cooled and discharged to give cocoalkyl-1,3-propanediamine 8.0 ethoxylate as the predominant species.

Example 5

Example 4 (262.4 g) was charged to a 2 liter reactor. After three vacuum and purge cycles with nitrogen the reactor was heated to 145° C. and ethylene oxide (18.7 g) was added at a steady rate over 14 minutes. The product was cooled and discharged to give cocoalkyl-1,3-propanediamine 9.0 ethoxylate as the predominant species.

Preparation of cocoalkylpolyamine alkoxylate Derivatives

Example 6

Quaternary amine Derivative of cocoalkylpolyamine

Example 1 (50 g, 0.11 mol) was placed in a 1 liter jacketed flask which was heated to 60° C. with circulating hot water. Deionised water (16.1 g) and anhydrous potassium carbonate (0.05 g, 0.05% w/w based upon reaction contents) were added to give a clear red homogeneous solution. Benzyl chloride (14.16 g, 0.11 mol) was then added drop wise over a period of 30 minutes with the temperature rising to 65° C. Once all of the benzyl chloride had been added, the ph of a 10% weight/volume (w/v) aqueous solution was measured to give a value of 8.76 and the temperature of the recirculating water was raised to 90-95° C. The reaction was maintained at this temperature for a total of 4 hours. pH was regularly monitored and maintained by the addition of 50% w/w potassium hydroxide solution throughout this heating stage maintaining the pH in the region of 7.4-8.0. The final material was seen to be a viscous waxy gel at 25° C. so to this was added deionised water (26.7 g) and the product was offloaded as a clear dark red solution. Overall yield of the product was approximately 89 g as a 60% active monobenzyl derivative in water.

Example 7

N-oxide Derivative of cocoalkylpolyamine

Example 1 (80 g, 0.18 mol) was placed in a jacketed flask along with deionised water (165.2 g). Dissolvine 50 sequestrant (0.09 g), and potassium hydrogen carbonate (1.43 g). The homogeneous solution was stirred whilst heating to 40° C. and the pH of a 10% w/v aqueous solution was measured to be less than 9.0. Hydrogen peroxide solution (40.6 g, 0.36 mol of a 30% w/v solution) was added over a period of 30 minutes with stirring and after the addition, the reaction was held at 40° C. for 5 hours. The residual peroxide was measured using peroxide test strips and the temperature was raised first to 60° C. then later to 70° C. The final pH (10% w/v aqueous solution) was found to be 8.1. The product (270 g) was eventually offloaded as a pale yellow aqueous solution at approximately 30% active matter.

Example 8

Betaine Derivative of cocalkylpoylamine

Example 1 (50 g, 0.11 mol) was placed in a jacketed flask along with deionised water (106.5 g) and the reaction was stirred and heated at 70° C. An 80% aqueous solution of monochloroacetic acid (13.22 g, 0.11 mol) was added followed by a 50% w/w solution of potassium hydroxide (12.55 g). The orange clear liquid was stirred for 20 minutes and the pH of a 10% w/v aqueous solution was measured to give a value of 9.62. Potassium hydroxide (50% w/w aqueous solution) was added dropwise to raise the pH to 10.0-10.5 before the temperature of the reaction was raised to 80° C. The reaction was continued to be heated at 80° C. whilst maintaining the pH between 10.0-10.5 for a total of 9 hours after which the pH was raised to 11.0-11.5 to hydrolyse any residual potassium monochloroacetate. The final clear red liquid was adjusted to pH 9.9-10.0 by addition of glacial acetic acid and the product was offloaded as a red solution (180 g) at approximately 31% active matter.

Example 9

Phosphate ester Derivative of cocoalkylpolyamine

Example 1 (50 g, 0.11 mol) was placed in a dry 250 ml necked round bottom flask fitted with a condenser, stirrer, thermocouple and nitrogen inlet. The flask was heated to 60-65° C. and 117% polyphosphoric acid was added with stirring. The reaction exothermed to 75° C. and the dark mobile liquid was stirred whilst being further heated to 120° C. After heating at 120° C. for 2.5 hours, the dark coloured solution was allowed to cool and when less than 60° C., deionised water (23.1 g) was added to dilute the material to approximately 70% active matter. The final product (77 g) was then offloaded as a mobile liquid/gel at 40° C.

Typical Preparation of glyphosate salt Compositions

The glyphosate salt concentrate was weighed in a 1 L volumetric flask to give the required loading of glyphosate acid present as the salt. For example, a 450 g/L glyphosate formulation was prepared by weighing 450 grams per liter (g/L) of glyphosate acid present as the potassium salt which is effectively 450 grams acid equivalent per liter (gae/L). The surfactants prepared in Examples 1-9 was added to the flask. Other additives such as glycerol was added to the formulation at this stage. Water was added to volume before the mixture was shaken vigorously.

TABLE 1

Compatibility study of Examples 1-9 in glyphosate.

| Composition Example | Glyphosate (gae/L)[a] | | | | | Example (g/L) | | | | | | | | | | Stable |
| --- | --- | --- | --- | --- | --- | --- | --- | --- | --- | --- | --- | --- | --- | --- | --- | --- |
| | K Salt | IPA Salt | MEA Salt | NH$_4$ Salt | Glycerol | 1 | 2 | 3 | 4 | 5 | 6 | 7 | 8 | 9 | Water | (Yes/No) |
| 10 | 450 | — | — | — | — | 100 | — | — | — | — | — | — | — | — | qv | Yes |
| 11 | 540 | — | — | — | — | 100 | — | — | — | — | — | — | — | — | qv | Yes |
| 12 | 600 | — | — | — | — | 100 | — | — | — | — | — | — | — | — | qv | Yes |
| 13 | — | 450 | — | — | — | 100 | — | — | — | — | — | — | — | — | qv | Yes |
| 14 | — | 540 | — | — | — | 100 | — | — | — | — | — | — | — | — | qv | Yes |
| 15 | — | — | 450 | — | — | 100 | — | — | — | — | — | — | — | — | qv | Yes |
| 16 | 450 | — | — | — | — | — | 100 | — | — | — | — | — | — | — | qv | Yes |
| 17 | 540 | — | — | — | — | — | 100 | — | — | — | — | — | — | — | qv | Yes |
| 18 | 600 | — | — | — | — | — | 100 | — | — | — | — | — | — | — | qv | Yes |
| 19 | — | 450 | — | — | — | — | 100 | — | — | — | — | — | — | — | qv | Yes |
| 20 | — | 540 | — | — | — | — | 100 | — | — | — | — | — | — | — | qv | Yes |
| 21 | — | — | 450 | — | — | — | 100 | — | — | — | — | — | — | — | qv | Yes |
| 22 | 450 | — | — | — | — | — | — | 100 | — | — | — | — | — | — | qv | Yes |
| 23 | 540 | — | — | — | — | — | — | 100 | — | — | — | — | — | — | qv | Yes |
| 24 | 540 | — | — | — | 30 | — | — | 70 | — | — | — | — | — | — | qv | Yes |
| 25 | 600 | — | — | — | — | — | — | 100 | — | — | — | — | — | — | qv | Yes |
| 26 | — | 450 | — | — | — | — | — | 100 | — | — | — | — | — | — | qv | Yes |
| 27 | — | 540 | — | — | — | — | — | 100 | — | — | — | — | — | — | qv | Yes |
| 28 | — | — | 450 | — | — | — | — | 100 | — | — | — | — | — | — | qv | Yes |
| 29 | 450 | — | — | — | — | — | — | — | 100 | — | — | — | — | — | qv | Yes |
| 30 | 540 | — | — | — | — | — | — | — | 100 | — | — | — | — | — | qv | Yes |
| 31 | 600 | — | — | — | — | — | — | — | 100 | — | — | — | — | — | qv | Yes |
| 32 | — | 450 | — | — | — | — | — | — | 100 | — | — | — | — | — | qv | Yes |
| 33 | — | 540 | — | — | — | — | — | — | 100 | — | — | — | — | — | qv | Yes |

TABLE 1-continued

Compatibility study of Examples 1-9 in glyphosate.

| Composition Example | Glyphosate (gae/L)[a] | | | | Glycerol | Example (g/L) | | | | | | | | | Water | Stable (Yes/No) |
|---|---|---|---|---|---|---|---|---|---|---|---|---|---|---|---|---|
| | K Salt | IPA Salt | MEA Salt | NH4 Salt | | 1 | 2 | 3 | 4 | 5 | 6 | 7 | 8 | 9 | | |
| 34 | — | — | 450 | — | — | — | — | — | 100 | — | — | — | — | — | qv | Yes |
| 35 | 450 | — | — | — | — | — | — | — | — | 100 | — | — | — | — | qv | No |
| 36 | 540 | — | — | — | — | — | — | — | — | 100 | — | — | — | — | qv | No |
| 37 | 600 | — | — | — | — | — | — | — | — | 100 | — | — | — | — | qv | No |
| 38 | — | 450 | — | — | — | — | — | — | — | 100 | — | — | — | — | qv | No |
| 39 | — | 540 | — | — | — | — | — | — | — | 100 | — | — | — | — | qv | No |
| 40 | — | — | 450 | — | — | — | — | — | — | 100 | — | — | — | — | qv | No |
| 41 | — | — | — | 360 | — | — | — | 100 | — | — | — | — | — | — | qv | Yes |
| 42 | 540 | — | — | — | — | — | — | — | — | — | 100 | — | — | — | qv | Yes |
| 43 | 540 | — | — | — | — | — | — | — | — | — | — | 162 | — | — | qv | Yes |
| 44 | 540 | — | — | — | — | — | — | — | — | — | — | — | 100 | — | qv | Yes |
| 45 | 540 | — | — | — | — | — | — | — | — | — | — | — | — | 100 | qv | Yes |

[a]Potassium (K), Isopropylamine (IPA), Monoethanolamine (MEA), Ammonium ($NH_4$)

Example 46

Pot Trial Protocol (i). Plant Propagation.

Oat seeds were sown to 3 centimeter (cm) depth and variegated thistle was sown to 1 cm depth in 10 cm diameter pots tilled with potting mix. One week after seedling emergence, seedlings were thinned for uniform size to one seedling per pot. Oats were grown in a temperature-controlled greenhouse (14-25° C.) for 8 days then outdoors for 13 days prior to spray application, to more closely simulate field conditions. Variegated thistle was grown in a temperature-controlled greenhouse (14-25° C.) for 14 days then outdoors for 23 days prior to spray application. After the application of herbicides the pots were returned to the greenhouse with harvested for fresh weight.

(ii). Herbicide Application.

Herbicide formulations were applied using an enclosed laboratory track-sprayer fitted with three 110° flat fan nozzles spaced at 50 cm intervals across the boom. The boom moved along a fixed track at 6 kilometers per hour, sprayed at a water volume of 64 Liters per hectare with a pressure of 200 kPa. For Standard 1, a current commercial herbicide was used (ROUNDUP® CT broadacre herbicide (containing glyphosate) that is commercially available from the Monsanto Company of St. Louis, Mo.).

(iii) Assessment.

Visual observations of % control were recorded 10 Days After Treatment (DAT) or 12 DAT. Seedlings were harvested by cutting foliage off at base immediately prior to weighing on a Sartorius Basic electronic balance (range 0-4100 g) 14 DA.

(iv). Statistical Analysis.

Data was analyzed using a factorial design with two factors, Formulation and Rate. 5% least significant differences (LSD) were calculated for the mean of each treatment. The greatest herbicidal effect is denoted with alpha code "a" when significantly different to other treatments, which are coded "b", "C", "d" etc. with decreasing.

(v). Results.

TABLE 2

Factorial Analysis of Variance & significant differences - Fresh weight (g) 14 DAT on Variegated thistle.

| Composition | Grams Active ingredient per hectare (gai/ha) | | | Formulation mean |
|---|---|---|---|---|
| | 40 | 80 | 160 | |
| UTC[a] | | 18.30 | | |
| Standard 1[b] | 8.72 v-A | 6.65 j-q | 4.62 bcd | 6.66 b-e |
| Standard 2[c] | 8.41 u-z | 6.06 g-m | 4.44 abc | 6.30 abc |
| Example 10 | 8.07 s-y | 6.05 f-m | 4.74 b-e | 6.29 abc |
| Rate mean | 8.40 c | 6.25 b | 4.60 a | |

[a]UTC: Untreated control,
[b]Standard 1: Commercial herbicide,
[c]Standard 2: 450 g/L glyphosate acid present as the potassium salt (450 gae/L) and blend of coco and tallowamine ethoxylates (100 g/L)

TABLE 3

Factorial Analysis of Variance table & significant differences - Fresh weight (g) 14 DAT on Oats.

| Composition | Grams Active ingredient per hectare (gai/ha) | | | Formulation mean |
|---|---|---|---|---|
| | 40 | 80 | 160 | |
| UTC[a] | | 4.28 | | |
| Standard 1[b] | 3.34 l-s | 1.07 a-d | 0.65 a | 1.69 ab |
| Standard 2[c] | 3.10 i-p | 1.06 a-d | 0.63 a | 1.60 ab |
| Example 10 | 3.99 t-w | 2.01 e-h | 1.05 abc | 2.35 de |
| Rate mean | 3.48 c | 1.38 b | 0.78 a | |

[a]UTC: Untreated control,
[b]Standard 1: Commercial herbicide,
[c]Standard 2: 450 g/L glyphosate acid present as the potassium salt (450 gae/L) and blend of coco and tallowamine ethoxylates (100 g/L)

TABLE 4

Summary table-ranking of formulations based on fresh weight formulation means.

| Composition | Variegated thistle Formulation mean[d] | Variegated thistle ranking | Oat Formulation mean[d] | Oat ranking | Combined ranking |
|---|---|---|---|---|---|
| Standard 2[c] | 6.30 abc | 2 | 1.60 ab | 1 | 3 |
| Example 10 | 6.29 abc | 1 | 2.35 de | 3 | 4 |
| Standard 1[b] | 6.66 b-e | 3 | 1.69 ab | 2 | 5 |
| UTC[a] | 18.30 | | 4.28 | | |

[a]UTC: Untreated control,
[b]Standard 1: Commercial herbicide,
[c]Standard 2: 450 g/L glyphosate acid present as the potassium salt (450 gae/L) and blend of coco and tallowamine ethoxylates (100 g/L).

Example 47

Field Trial Protocol (i). Site Information and Herbicide Application.

Treatments were applied to awnless barnyard grass (*Echinochloa colona*) and red pigweed (*Portulaca oleracea*) in a no-till fallow to 2.5×10 meter plots using a 2 meter hand held boom equipped with 4 XR110015 flat fan nozzles calibrated to deliver 80 Liters per hectare at a ground speed of 6 kilometers per hour and a pressure at the nozzle of 160 kPa. Standard 3 was ROUNDUP POWERMAX® agricultural herbicide formulation which is commercially available from the Monsanto Company of St. Louis, Mo. Weather details at application are summarised in Table 5. Conditions were favourable for plant growth at the time of application though soil moisture had declined significantly over the days leading up to treatment.

TABLE 5

Application conditions

| Temperature | Relative humidity | Cloud | Wind speed/direction |
|---|---|---|---|
| 26-29° C. | 50-46% | 0 | 12-14 kPa |

The weed spectrum targeted was dominated by liverseed (*urochloa*) grass with awnless barnyard grass and red pigweed being less prominent (Table 6).

TABLE 6

Weed details at application

| Weed common name | Botanical name | Growth stage | Size |
|---|---|---|---|
| Liverseed (*urochloa*) grass | *Urochloa panicoides* | 4 leaf-2 tillers | 5-12 cm |
| Awnless barnyard grass | *Echinochloa colona* | 2-6 leaf | 2-7 cm |
| Red pigweed | *Portulaca oleracea* | Vegetative | 3-8 cm diameter |

(ii). Assessments

Assessments of brownout were undertaken 6 and 14 DAT using a subjective rating where 0=no effect and 100=complete brownout. A subjective assessment of control was carried out 21 and 28 (liverseed grass only) DAT using a 0-100 scale where 0=no control and 100=complete control. A value of 85 and above was considered as commercially acceptable. Data was analysed using ARM®7 software with treatment means being separated on the basis of Duncan's New Multiple Range Test at the 5% level of significance. Treatment means are considered statistically similar where they share common letters following the value shown (iii). Seasonal Conditions.

Seasonal conditions were very warm to hot leading up to and following application. While adequate soil moisture was present at the time of treatment, this declined in a few days and unsprayed plants exhibited a moderate level of moisture stress at the time of final assessment.

(iv). Results.

TABLE 7

Brownout rate of composition prepared in Examples 11, 23, 24 and 43

| | | | Pest Name | | | | | |
|---|---|---|---|---|---|---|---|---|
| | | | Liverseed grass | Liverseed grass | Liverseed grass | Junglerice | Red pigweed | Liverseed grass |
| | | | | | Days After Treatment | | | |
| | | | 6 | 14 | 21 | 21 | 21 | 28 |
| Composition | Rate | Unit | | | % Brownout[a] | | | |
| UTC[b] | | | 0.00 | 0.00 | 0.00 | 0.00 | 0.00 | 0.00 |
| Standard 3[c] | 189 | G AE/HA | 60.00 c-h | 76.67 cd | 80.00 b | 70.01 b-h | 59.07 gh | 81.00 b |
| | 378 | G AE/HA | 66.67 b-e | 93.33 ab | 97.33 a | 90.01 ab | 95.00 a | 98.00 a |
| Example 11 | 189 | G AE/HA | 43.33 hij | 71.67 def | 80.00 b | 60.00 f-j | 73.33 def | 75.00 bcd |
| | 378 | G AE/HA | 81.67 ab | 94.67 ab | 98.33 a | 91.67 a | 91.67 ab | 95.33 a |
| Example 23 | 189 | G AE/HA | 43.33 hij | 71.67 def | 75.00 b | 63.33 d-i | 76.67 cd | 70.00 c-f |
| | 378 | G AE/HA | 68.33 bcd | 94.67 ab | 96.00 a | 88.33 ab | 93.33 ab | 94.00 a |
| Example 24 | 189 | G AE/HA | 40.00 ij | 65.00 d-g | 72.33 b | 50.01 hij | 74.07 de | 61.67 f |
| | 378 | G AE/HA | 66.67 b-c | 85.00 bc | 93.33 a | 76.67 a-g | 90.88 ab | 91.67 a |
| Example 43 | 189 | G AE/HA | 40.00 ij | 71.67 def | 70.00 b | 51.67 hij | 68.33 def | 73.33 b-c |
| | 189 | G AE/HA | 75.00 abc | 93.33 ab | 99.33 a | 81.67 a-e | 95.00 a | 98.33 a |

[a]Values separated, by different letters are statistically different at the 5% level of probability according to the Duncan's New MRT Test,
[b]UTC: Untreated control,
[c]Standard 3: Commercial herbicide.

Although the present invention and its advantages have been described in detail, it should be understood that various changes, substitutions and alterations may be made herein without departing from the spirit and scope of the invention as defined by the appended claims.

Where the terms "comprise", "comprises", "comprised" or "comprising" are used in this specification, they are to be interpreted as specifying the presence of the stated features, integers, steps or components referred to, but not to, preclude the presence or addition of one or more other feature, integer, step, component or group thereof.

What is claimed is:

1. An agricultural composition comprising:
   a) an agrochemical active ingredient; and
   b) at least one cocoalkylpolyamine alkoxylate agent, wherein the at least one cocoalkylpolyamine alkoxylate agent is a derivatized form selected from the group consisting of:
   a benzyl quaternary amine derivative having the formula:

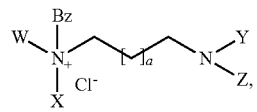

a phosphate ester derivative having the formula:

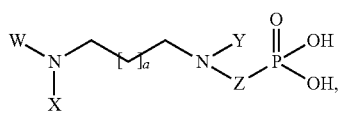

a sulfate derivative having the formula:

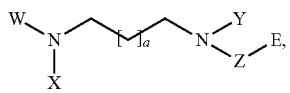

a carboxylic acid derivative having the formula:

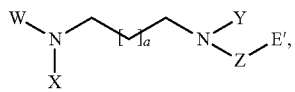

and a combination thereof,
wherein W is a coco hydrocarbyl group, X and Y are alkylene oxide groups, Z is selected from the group consisting of one or more ethylene oxide units, one or more propylene oxide units, and a combination thereof, E is a sulfate group, E' is a carboxylic acid group and a is an integer from 0 to 2 and the concentration of the agrochemical active ingredient is at least 450 grams acid equivalent per liter (gae/L).

2. The composition according to claim 1, wherein the agrochemical active ingredient includes glyphosate or a salt thereof, the salt selected from the group consisting of an ammonium, an alkylamine, an alkanolamine, an alkylsulfonium, an alkali metal and a combination thereof.

3. The composition according to claim 1, wherein the agrochemical active ingredient includes a water soluble fertilizer.

4. The composition according to claim 1, further comprising at least one additive.

5. The composition according to claim 4, wherein the at least one additive is selected from the group consisting of: an antifoaming agent, a compatibilizing agent, a sequestering agent, a neutralizing agent, a dye, an odorant, a penetration aid, a wetting agent, a spreading agent, a thickening agent, a freeze point depressant, a humectant, a conditioner, an antimicrobial agent, a crop oil, and a combination thereof.

6. The composition according to claim 1, wherein the concentration of the agrochemical active ingredient is at least 540 grams acid equivalent per liter (gae/L).

7. The composition according to claim 1, wherein the concentration of the agrochemical active ingredient is at least 600 grams acid equivalent per liter (gae/L).

8. A method of treatment of vegetation, comprising contacting the agricultural composition of claim 1 to with vegetation.

9. A method of making a high strength aqueous solution comprising contacting an agrochemical active ingredient and at least one cocoalkylpolyamine alkoxylate agent, wherein the at least one cocoalkylpolyamine alkoxylate agent is a derivatized form selected from the group consisting of:

a benzyl quaternary amine derivative having the formula:

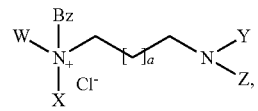

a phosphate ester derivative having the formula:

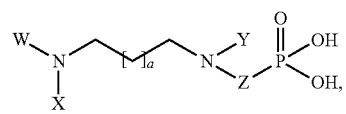

a sulfate derivative having the formula:

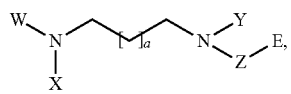

a carboxylic acid derivative having the formula:

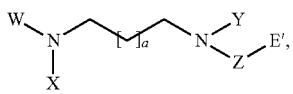

and a combination thereof,
wherein W is a coco hydrocarbyl group, X and Y are alkylene oxide groups, Z is selected from the group consisting of one or more ethylene oxide units, one or more propylene oxide units, and a combination thereof, E is a sulfate group, E' is a carboxylic acid group and a is an integer from 0 to 2 and the concentration of the agrochemical active ingredient is at least 450 grams acid equivalent per liter (gae/L).

10. The method according to claim 9, wherein the agrochemical active ingredient is a water soluble herbicide selected from the group consisting of a bipyridyl herbicide, a phenoxy ester herbicide, a pyridinylphenoxy herbicide, a salt thereof, and a combination thereof.

11. The method according to claim 9, wherein the agrochemical active ingredient includes glyphosate or a salt thereof, the salt selected from the group consisting of an ammonium, an alkylamine, an alkanolamine, an alkylsulfonium, an alkali metal and a combination thereof.

12. The method according to claim 9, wherein the agrochemical active ingredient includes a water soluble fertilizer.

* * * * *